United States Patent
Patel-Framroze

(10) Patent No.: US 7,868,165 B2
(45) Date of Patent: Jan. 11, 2011

(54) PROCESS FOR THE ISOLATION AND STABILIZATION OF LOW-MOLECULAR WEIGHT AMINOGLYCANS FORM WASTE EGG SHELLS

(76) Inventor: Bomi Patel-Framroze, 3, Shree Sadan, 4A, Carmichael Road, Mumbai, MH (IN) 400 026

( * ) Notice: Subject to any disclaimer, the term of this patent is extended or adjusted under 35 U.S.C. 154(b) by 542 days.

(21) Appl. No.: 11/895,500

(22) Filed: Aug. 27, 2007

(65) Prior Publication Data
US 2008/0051368 A1     Feb. 28, 2008

Related U.S. Application Data

(63) Continuation-in-part of application No. 11/277,489, filed on Mar. 25, 2006, now abandoned.

(51) Int. Cl.
*C08B 37/00* (2006.01)
*C07H 5/06* (2006.01)

(52) U.S. Cl. .................... 536/55.1; 536/123; 536/123.1

(58) Field of Classification Search ........................ None
See application file for complete search history.

(56) References Cited

U.S. PATENT DOCUMENTS

| | | | | |
|---|---|---|---|---|
| 5,888,984 | A * | 3/1999 | Brown | 514/54 |
| 6,946,551 | B2 * | 9/2005 | Long et al. | 536/55.3 |
| 7,002,007 | B2 * | 2/2006 | Berbaum | 536/127 |
| 7,584,909 | B2 * | 9/2009 | Vlad | 241/2 |
| 2004/0180851 | A1 | 9/2004 | Long et al. | |

FOREIGN PATENT DOCUMENTS

EP     1707578 A2     10/2006

OTHER PUBLICATIONS

T. Nakano et al, Extraction of Glycosaminoglycans from Chicken Eggshell, Poultry Science, 2001, 681-684, 80, Poultry Science Association, Inc, USA.

* cited by examiner

Primary Examiner—Eric S Olson

(57) ABSTRACT

A process for the isolation of low-molecular weight aminoglycan compound of formula I made up of alternating glucuronic acid and N-acetyl glucosamine units; from a hitherto unexploited natural source of waste egg shells; which process comprises the steps of:

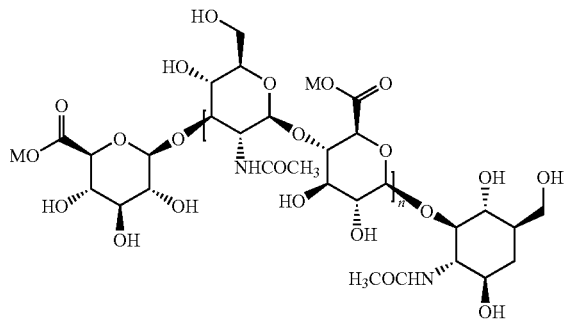

I wherein M may be at one or more instances Na, Ca, K, Mg: and
n is an integer between 20 and 40:

(a) pre-preparation of the waste egg-shells for extraction of the embryonic low molecular weight aminoglycan compound of formula I using a polar organic solvent in water;
(b) extraction of the low molecular weight aminoglycan compound of formula I as its water soluble salt using an aqueous polar salt solution;
(c) isolation of a purified low molecular weight aminoglycan compound of formula I by gel formation out of the aqueous salt mixture by using a polar organic solvent followed by filtration or centrifuging;
(d) stabilization of the isolated aminoglycan extract by sequential introduction of organic oils into a semi-dried gel to form the aminoglycan compound of formula I.

6 Claims, No Drawings

PROCESS FOR THE ISOLATION AND STABILIZATION OF LOW-MOLECULAR WEIGHT AMINOGLYCANS FORM WASTE EGG SHELLS

CROSS-REFERENCE TO RELATED APPLICATION

This application is a continuation-in-part of U.S. application Ser. No. 11/277,489, filed on 25 Mar. 2006 now abandoned and is still pending and is incorporated by reference herein.

FIELD OF THE INVENTION

Embodiments of the invention relate to a simple and efficient method of isolating and stabilizing ultra low molecular weight aminoglycans from waste egg shells.

BACKGROUND OF THE INVENTION

Embodiments of the invention relate to a process for isolating, stabilizing and formulating low molecular weight aminoglycans from waste egg shells. The aminolycan extract is useful for the preparation of cosmetic creams with skin moisturizing and anti-wrinkle properties.

Nakano et al. (*Poult Sci.* (1991), Vol. 70(12), pp. 2524-8) have shown that the chemical composition of glycosaminoglycan fractions from the comb and wattle of single comb white Leghorn roosters consist of very large molecular weight glycosaminoglycans that have applications in cartilage replacement therapy.

Balazs et al (U.S. Pat. No. 4,141,973) has described a process to isolate pure hyaluronic acid from animal tissue bearing molecular weights in the range of 1 MD to 6 MD useful as a replacement for synovial fluids and vitreous humor.

Heaney et al. (*Biochim Biophys Acta.* (1976), Vol. 18; 451(1), pp. 133-42) have shown that the organic part of the chicken's egg shell consists of collagen, proteins and polysaccharides which are probably present as glycoproteins and glycosaminoglycans. They further identified the organic components by chromatography to yield glycosaminoglycans with a minimum molecular weight of 30,000 Daltons. Sedimentation velocity analysis in a density gradient, showed that the polysaccharides contained equimolar amounts of glucosamine (36.3% s/w) and glucuronic acid 35.6% w/w. Identification of the degradation products showed the glycosaminoglycan to be mainly hyaluronic acid.

Stahl et al (U.S. Pat. No. 6,537,795) have described a process to produce and isolate aminoglycans from cultivated strains of streptococci fermentation. These aminoglycans are characterized by extreme high molecular weights above 6 MD and are useful for cartilage replacement therapy.

Related processes for isolations and purifications of glycosaminoglycans from other natural sources and animal tissues may also be found in U.S. Pat. Nos. 5,824,658, 6,660,853 and 6,451,326. The references discussed within these patents are hereby incorporated herein by reference.

SUMMARY OF THE INVENTION

Embodiments of the invention provide a novel process for the isolation of low-molecular weight aminoglycan compounds of formula I made up of alternating glucuronic acid and N-acetyl glucosamine units from a hitherto unknown natural source of waste egg shells;

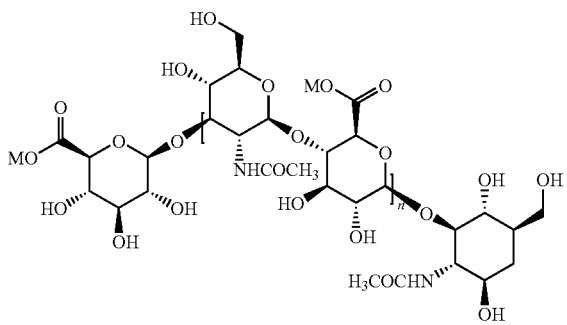

wherein M may be at one or more instances Na, Ca, K, Mg; and n is an integer between 20 and 40;

comprising the steps of:

(a) pre-preparation of the waste egg-shells for extraction of the embryonic low molecular weight aminoglycan compound of formula I using a polar organic solvent dissolved in water;

(b) extraction of the low molecular weight aminoglycan compound of formula I as its water soluble salt using an aqueous polar salt solution;

(c) isolation of a purified low molecular weight aminoglycan compound of formula I by gel formation out of the aqueous salt mixture by using a polar organic solvent followed by filtration or centrifuging;

(d) stabilization of the isolated aminoglycan extract by sequential introduction of organic oils into a semi-dried gel to form ordered sheets of aminoglycan compound of formula I with no visible cross-linking of the carbohydrate polymer.

Embodiments of the invention relate more particularly to step (b), wherein the aqueous polar salt solution can be the sodium, potassium, calcium or magnesium salts of citrate, glutamate, acetate, pyrrolidone carbonate, tartrate, glycinate, sulfate, sulfite, nitrate, carbonate, oxalate to yield a solution containing aminoglycan compound of formula I, which is suitable for selective gelation and isolation.

The process described herein is a novel method to selectively and simply yield a low-molecular weight aminoglycan compound of formula I from waste egg shells. More specifically, the process of the invention, compared to the procedures for isolating aminoglycans disclosed in the prior art, are differentiated by;

a) identification of a novel hitherto unused source, egg shell waste, which is otherwise difficult to dispose of and causes significant negative impact to the environment, b) contains very low concentrations of detrimental proteins and nucleotides, c) requires no expensive and inefficient separations of organic and inorganic materials from the egg shell waste, d) are simpler extractions involving mild reagents and solvents materials; and e) requires no acetylation or other derivatization for example using acetic anhydride and sulfuric acid as described in U.S. Pat. No. 5,679,657 to achieve the desired viscosity and threading properties needed for cosmetic applications.

The aminoglycan compound of formula I is of an unusually low molecular weight and is yet stabilized without derivatization to show excellent dermal penetration to reduce surface wrinkles in skin and exhibit an excellent softening and moisturizing effect as well.

DETAILED DESCRIPTION OF THE INVENTION

Egg shell waste produced from the egg processing industry is usually washed with solvents and treated to eliminate unpleasant smells before being used as landfill. The calcium carbonate of the shells is only usable upon extensive separation and cleaning procedures which makes the process commercially uneconomical. There is no specific need to pulverize the egg shells within a narrowly bound range either since the process of the present invention is not dependent on the separation of the inner membrane from the egg shell as in the complex process and equipment described by MacNeil (U.S. Pat. No. 6,176,376) to obtain pure calcium carbonate.

We have identified a process to selectively isolate valuable organic compounds, specifically aminoglycan compound of formula I from crushed egg shells without expensive separation of the organic and inorganic components.

Crushed egg shells may be treated with warm water or warm 5% ethanol solution and filtered to remove adhered organic wastes from the surface of the shells. The ratio of organic mass to calcium carbonate may be between 1% to 15% w/w. Greater ratios of organic mass would indicate unwashed egg mass present in the crushed egg shells which can lead to the presence of detrimental protein and nucleotide products in the aminoglycan extract. It is noted that unlike other sources of aminoglycans such as animal tissue and fermentation broths as known in the prior art, the use of egg shell waste as shown herein is unique in the absence of significant antigenic protein and nucleotide components in the extracted media leading to easier methods of extracting purified aminoglycan compound of formula I. The egg shells may be additionally pre-treated with ultraviolet light to destroy microbes which may be present even after liquid cleaning.

The next step comprises treatment of the above egg shell mass to a highly selective extraction of the carbohydrate component in the form of its water-soluble salt. The process involves suspending the egg shell mass in 1:2 to 1:10 volume of solution containing 5% to 40% by weight citrate, glutamate, acetate, pyrrolidonecarbonate, tartrate, glycinate, sulfate, sulfite, nitrate, carbonate and oxalate salts of sodium, potassium, calcium or magnesium or a combination of the above salt solutions as needed. More specifically the monovalent salts of organic acids are preferred. The suspension is held for 1 to 24 hours, more preferably for 6 to 12 hours, with periodic vigorous shaking at temperatures ranging between 10° C. and 35° C. The suspension is subsequently filtered or centrifuged to remove the aqueous solution containing the appropriate salt of the aminoglycan compound of formula I. The egg shell mass thus separated shows a much looser binding of the membranes to the egg shell and hence, may be more easily treated using processes known in the art to separate the pure calcium carbonate containing egg shell from the organic residue.

The next step comprises the gel precipitation of the aminoglycan compound of formula I in its appropriate salt form from the aqueous solution. The process involves reducing the polarity of the aqueous solution and hence, the solubility of the aminoglycan compound by the sequential addition of any aqueous miscible organic solvent such as alcohols, acetone, dimethylformamide, N-methylpyrrolidinone or 1,4-dioxane. The organic solvent is added in lots with mild stirring and cooling to maintain the temperature of the reaction between 20° C. to 25° C. to yield a white gel formation suspended in the aqueous layer. The solution is allowed to stand for 2 to 24 hours until gelation is complete and subsequently filtered or centrifuged to yield a semi-dry extract of aminoglycan compound of formula I. It is important to not allow the extract to be completely dried since a certain amount of the aqueous phase is required during the stabilization process carried out next.

The final step comprises stabilization of the low-molecular weight aminoglycan compound of formula I by ordering the molecules in a lipophilic environment to prevent cross-linking which is characteristic of non-acetylated and low-molecular weight aminoglycans as described in the prior art. The process involves a sequential addition of two oils whose total weight ratio to the aminoglycan extract is between 1:0.5 and 1:3 and wherein the individual oil ratios between the two oils are 3:1 to 8:1. The first oils should be more hydrophobic in nature and may be selected from oils found typically in plant nuts. Specifically almond oil and jojoba oil are more preferred as the first oil. The second oil component should be more hydrophilic in nature and may be selected from oils typical isolated from herbs and spices from the vegetative parts of plants. Specifically sage oil, rosemary oil and lavender oil are more preferred as the second oil.

The molecular weight of aminoglycan compound of formula I thus isolated is difficult to measure directly and hence, I have relied on the measure of intrinsic viscosity to determine the molecular weight (Laurent et al, *Biochimica et Biophysica Acta*, Vol. 42, pg. 476 (1960)). The intrinsic viscosities of various solutions containing aminoglycan compound of formula I were found to lie between 4 cm3/gm and 7 cm3/gm and when plotted against standard solutions of hyaluronic acid salts (Mol. Wt. approximately 1.2 MD) led to the assignment of a unique natural ultra low molecular weight for aminoglycan compound of formula I between the range of 15,000 Daltons and 28,000 Daltons. An ultra low molecular weight aminoglycan compound of formula I from a natural source has not been previously described in the prior art (for example as summarized by Balazs et al. in U.S. Pat. No. 4,582,865).

Experimental Results

Example 1

500 g of pre-treated egg shell waste with approximately 10% organic content was added to an open mouth glass container with a screw top. To this was added 750 ml of a 5% aqueous solution of sodium citrate and the container was sealed and placed on a shaker for 24 hours at moderate speeds. After 24 hours the entire mixture was transferred into a filter funnel and the solid egg shell waste was separated from the aqueous suspension. The solids were washed with 1×250 ml of 5% aqueous solution of sodium citrate and the combined aqueous layers were washed once with 250 ml of methylene chloride to remove potential proteinaceous matter and the aqueous layer was then transferred to a 2 L beaker. The beaker was placed in a cold water bath and a slow addition of absolute methanol was initiated with slow stirring. After about 200 ml of methanol addition was completed, a cloudy white precipitate began to form and the stirring was stopped. An equal additional quantity of methanol was added slowly and the beaker was allowed to stand for 12 hours to make sure gelation was complete. The entire mass was transferred to a filter funnel and filtered to give a cream colored gel of aminoglycan compound of formula I. The precipitate was dried until a moisture content of 5-7% was measured. The final weight of the gel of aminoglycan compound of formula I was 42 g.

Example 2

The gel material containing aminoglycan compound of formula I from Example I was mixed with 4 g of jojoba oil at 15°-20° C. and stirred vigorously for 20 minutes. The resultant gel was warmed to 25° C. and allowed to gently stir for 1 hour. To this mass was added 1 g of sage oil and the resultant gel was further stirred gently for 10 minutes. The gel was then allowed to slowly cool to 10° C. over 4 hours to obtain the aminoglycan compound of formula I, which is stable in the absence of circulating air at room temperature for at least 3 months.

Example 3

The above example 1 was repeated with a 10% aqueous solution of potassium tartrate to yield 46 g of the gel of aminoglycan compounds of formula I.

Example 4

The above example 1 was repeated with a 20% solution of sodium acetate to yield 43 g of the gel of aminoglycan compound of formula I.

Example 5

The above example 1 was repeated except that ethanol was used instead of methanol for complete gel formation to yield 47 g of the gel of aminoglycan compound of formula I.

Example 6

The above example 1 was repeated except that ethanol was used instead of methanol for complete gel formation to yield 41 g of the gel of aminoglycan compound of formula I.

Example 7

The above example 1 was repeated with a 10% solution of sodium carbonate to yield 24 g of the gel of aminoglycan compound of formula I.

Example 8

The above example 1 was repeated with a 25% solution of calcium carbonate to yield 14 g of the gel of aminoglycan compound of formula I.

Example 9

10 g of the above stabilized gel made as per the procedure shown in Example 2 is added to 50 ml of distilled water containing 3 ml of glycerin and stirred to a uniform suspension. To this suspension is added a melt consisting of 10 g of emulsifying wax, 10 g of paraffin wax, 4 g of white beeswax and 13 g of a mix of cosmetically useful plant oils such as almond, lavender, sandalwood and walnut and the mixture stirred vigorously to give a uniform cream with excellent physical characteristics and anti-wrinkle properties.

With respect to the above isolated and stabilized gels of aminoglycan compound of formula I the following analytical and usefulness tests were conducted.

Absence of Chondroitin Sulfate

It is known in the prior art that all commercial sources of aminoglycans are usually closely associated with other tissue components such as Chondroitin sulfate (Arkins and Sheehan, Structure of Hyaluronic Acid, Nature New Biol 235, 253, 1972 and Bettelheim and Philpott, Electron Microscopic Studies of Hyaluronic Acid—Protein Gels, *Biochim Biophys Acta* 34, 124, 1959). The gel extract isolated as per the methods described above contains less than 2% Chondroitin sulfate probably due to the low association possible with the extra small size of the aminoglycan compound of formula I isolated herein.

Absence of Proteins

Since proteins are potentially antigenic, it is essential for cosmetic formulations to isolate any aminoglycan gel essentially free of proteins. The gel extract from Example 1 was subjected to the highly sensitive colorimetric test for detecting the presence of proteins described by Lowry et al. (*J. Biol. Chem.*, 193, 265-275, 1951). No positive result was obtained indicating the presence of proteins to be less than 0.1% by weight.

The absence of any appreciable protein concentration is a distinct difference from other glycosaminoglycan compounds isolated from other natural sources such as Rooster Comb and fermentation broths. It has been reported (Kludas, U.S. Pat. No. 5,055,298) that these aminoglycans are usually covalently linked with proteins to form proteoglycans. Clinically relevant removal of all of these proteins, which are not components of human skin, has proved to be difficult and not easily accomplished. The presence of these proteins in various other aminoglycan extracts has been identified as a cause of significant inflammatory responses on skin surfaces, making their use in cosmetic formulations challenging.

Absence of Nucleotides

Ultraviolet spectroscopy has been used to show the absence of potentially antigenic DNA and RNA nucleotides in the aminoglycan compound of formula I extracted herein. A 1% solution of the aminoglycan extract from Example 1 in 10% sodium chloride solution was prepared. This solution was subjected to ultraviolet spectroscopy at 257 nm to measure the level of nucleotides in the solution. The absence of any absorption at this wavelength was taken as a measure of the absence of nucleotides in the aminoglycan extract from Example 1.

Viscosity

A small sample of the gel was freeze-dried to give a white solid with a thread like structure which slowly dissolved in water. A solution of 1 mg of the powder was made up in 1000 ml of a phosphate buffer at pH 7. Viscosity was determined with an Ostwald viscosimeter at a temperature of 25 C. The relative viscosity of the solution was measured as 0.76 to 0.80. When compared to aminoglycans of known higher molecular weight this viscosity measurement leads to molecular weights for aminoglycan compound of formula I between 15 kD and 28 kD.

Glucosamine Presence

The presence of glucosamine in the aminoglycan compound of formula I was determined by the method of Elson and Morgan (Biochem J, Vol. 27, (1933), p. 1894,) on material that had been hydrolyzed for 6 hours with 5N hydrochloric acid at 100 C. and evaporated to dryness. The glucosamine content of the aminoglycan compound of formula I was between 38% and 41% which matches the expected calculated value.

Presence of Uronic Acid:

The presence of uronic acid in the aminoglycan compound of formula I was determined by digestion with hyaluronidase. The extracted aminoglycan compound of formula I was washed with distilled water and hydrolysed with *Streptomyces* hyaluronidase (1 mg of enzyme/g of aminoglycan) in 10 ml of 10 mM $CaCl_2$/50 mM-Tris/HCl buffer, pH 7.6, for 48 h at 37° C. The proteinase inhibitors namely phenylmethanesulphonyl fluoride (2 mM) and N-ethylmaleimide (10 mM) were added to the samples to inhibit non-specific proteolysis. The hydrolysis was stopped by adding urea to 6M final concentration. The hydrolysate was centrifuged at 4000 g and the supernatant (hyaluronidase digest) was removed and matched against standard uronic acid by HPLC (High Performance Liquid Chromatography) analysis.

Thread Forming Ability

It is well documented in the prior art that the higher the thread forming ability the more moisturizing is the effect of the aminoglycan. Many derivatives of high and medium molecular weight aminoglycans such as acetylation and co-polymerization (U.S. Pat. No. 5,679,657) have been used to increase the intrinsic threading value of aminoglycans isolated from animal and bacterial sources. It is unexpectedly observed that the ultra low molecular weight aminoglycan compound of formula I isolated herein shows a remarkably high thread forming ability and may account for part of the high anti-wrinkle effects observed. In a humidity chamber at a temperature of 25° C. and relative humidity of 50%, 1 cm of a glass rod was immersed in a 1% aqueous solution of aminoglycan extract from Example 1 and the thread length obtained upon lowering the beaker at a velocity of 10 cm/min was observed. The thread length of the aminoglycan of this invention was observed to be between 2.8 cm and 3.5 cm which is considerably longer than the 0.8 cm to 1.3 cm observed for commercially available sodium hyaluronate and even better than the lengths observed for derivatized aminoglycans.

Anti-Wrinkle Properties

The anti-wrinkle properties of the cream produced as per the method described in Example 9 was tested using a 3D imaging system to measure depths of surface wrinkles. The method described by S. Jaspers et al, ("Microtopometry Measurement of Human Skin in vivo by a new Digital Optical Projection System", Preprints 5th Congress of the International Society for Skin Imaging, Wien 1997) was used to show a 25% to 38% reduction in wrinkle depth after 4 weeks of daily use.

I claim:

1. A process for the isolation of low-molecular weight aminoglycan compounds of formula I from waste egg shells;

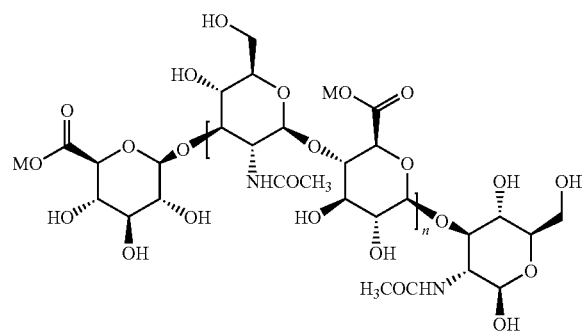

I wherein M may be at one or more instances Na, Ca, K, Mg; and n is an integer between 20 and 40, said process comprising the steps of:

(a) pre-preparation of the waste egg-shells for extraction of the embryonic low molecular weight aminoglycan compound of formula I using a polar organic solvent in water, wherein the pretreated egg shells are mixed thoroughly with a polar organic solvent in water at temperatures between 25° C. and 40° C. for 1 hour to 4 hours, followed by decantation of the supernatant and the eggshells carried forward for extraction;

(b) extraction of the low molecular weight aminoglycan compound of formula I as its water soluble salt using an aqueous polar salt solution, wherein the eggshells from step (a) are vigorously shaken with the aqueous polar salt solution at 25° C. to 40° C. for 6 to 24 hours, followed by decantation, filtration or centrifugation to collect the aqueous layer containing the dissolved aminoglycan compound of formula I;

(c) isolation of the purified low molecular weight aminoglycan compound of formula I by gel formation out of the aqueous salt mixture by using a polar organic solvent, wherein the solution from step (b) is subjected to sequential step wise addition of the polar organic solvent in an amount between 75% and 150% volume/volume of the polar organic solvent between 10° C. and 20° C. in 1 hour to 2 hours and the gel formed is allowed to stand for 4 hours to 12 hours to complete precipitation, followed by decantation, filtration or centrifugation to isolate semi dried aminoglycan compound of formula I containing between 4% to 8% moisture;

(d) stabilization of the isolated aminoglycan compound of formula I from step (c) by sequential introduction of organic oils into the semi-dried gel to form ordered sheets of aminoglycan compound of formula I.

2. The process as claimed in claim 1, wherein the polar organic solvent used in step (a) is selected from the group consisting of an alcohol, acetone, methyl ethyl ketone or 1,4-dioxane.

3. The process as claimed in claim 1, wherein the said aqueous polar salt solution is an organic acid salt selected from the group consisting of sodium, potassium, calcium or magnesium salt of citrate, glutamate, acetate, pyrrolidone carbonate, tartrate, glycinate, sulfate sulfite, nitrate, carbonate or oxalate.

4. The process as claimed in claim 1, wherein the polar organic solvent used in step (c) is selected from methanol, ethanol, propanol or butanol, or an organic ether selected from diethylether, tetrahydrofuran, methylal or ethylal.

5. The process as claimed in claim 1, wherein the oils used in step (d) are selected from group consisting of jojoba oil, almond oil, sage oil, rosemary oil, lavender oil, sandalwood oil or aloe oil.

6. The process as claimed in claim 1 further comprising adding at least one pharmaceutically acceptable excipient to the stabilized aminoglycan compound of formula I obtained in step (d) to form a composition having anti-wrinkle properties.

* * * * *